United States Patent [19]

Mendiratta et al.

[11] Patent Number: 4,461,915
[45] Date of Patent: Jul. 24, 1984

[54] PURIFICATION OF BISPHENOL-A

[75] Inventors: Ashok K. Mendiratta, Schenectady; Wayne F. Morgan, Mechanicville, both of N.Y.

[73] Assignee: General Electric Company, Schenectady, N.Y.

[21] Appl. No.: 443,344

[22] Filed: Nov. 15, 1982

[51] Int. Cl.³ ............................................. C07C 37/84
[52] U.S. Cl. .................................................... 568/724
[58] Field of Search ......................................... 568/724

[56] References Cited

U.S. PATENT DOCUMENTS

| 2,959,622 | 11/1906 | Grimme et al. | 568/724 |
|---|---|---|---|
| 3,326,986 | 6/1967 | Dugan et al. | 568/724 |
| 3,393,622 | 2/1970 | Ornstein et al. | 568/724 |
| 3,972,950 | 8/1976 | Kwantes | 568/724 |
| 4,079,087 | 3/1978 | Sun | 568/724 |
| 4,192,955 | 3/1980 | Reinitz | 568/724 |
| 4,212,997 | 7/1980 | Adams | 568/724 |
| 4,294,993 | 10/1981 | Li | 568/724 |
| 4,324,926 | 4/1982 | Demler et al. | 568/724 |

FOREIGN PATENT DOCUMENTS

| 6883099 | 6/1964 | Canada | 568/724 |
|---|---|---|---|
| 795236 | 5/1958 | United Kingdom | 568/724 |
| 946322 | 1/1964 | United Kingdom | 568/724 |
| 975863 | 11/1964 | United Kingdom | 568/724 |
| 570589 | 8/1977 | U.S.S.R. | 568/724 |

Primary Examiner—Werren B. Lone
Attorney, Agent, or Firm—Richard J. Traverso; James C. Davis, Jr.; James Magee, Jr.

[57] ABSTRACT

A method for purifying bisphenol-A involving aqueous crystallization of impure bisphenol-A followed by in-situ treatment of the water/bisphenol-A crystal slurry with an organic washing solvent is presented. The purified bisphenol-A is then either removed from the crystal slurry or melted so the purification process can be repeated before separating the purified bisphenol-A.

6 Claims, No Drawings

PURIFICATION OF BISPHENOL-A

BACKGROUND OF THE INVENTION

This invention is concerned with the purification of 2,2-bis(4-hydroxyphenyl) propane (hereinafter identified as "bisphenol-A" or "BPA"). More particularly, the invention is directed to a method for recovering bisphenol-A in a purified state from crude bisphenol-A.

Crude bisphenol-A is the isolated product of commercial processes for preparing bisphenol-A. It is a mixture of bisphenol-A and impurities derived from the BPA synthesis reaction. An example of BPA synthesis reaction is the acid-catalyzed condensation of phenol and acetone where phenol and acetone react in the presence of an acidic material such as sulfuric acid, hydrochloric acid, cation exchange resin, etc.

The crude bisphenol-A produced contains undesirable impurities such as the 2-(4-hydroxyphenyl)-2-(2-hydroxyphenyl) propane (hereinafter identified as "o,p-isomer") having the formula

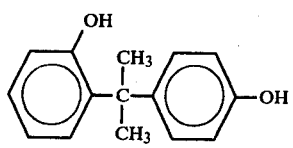

as well as other impurities including phenol itself used in making the bisphenol-A, a trishydroxyphenyl compound of the formula

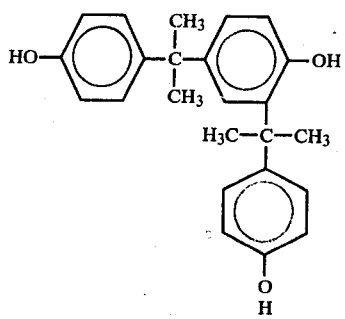

(hereinafter identified as "BPX-1"), small amounts of other impurities such as the two compounds having the formulas

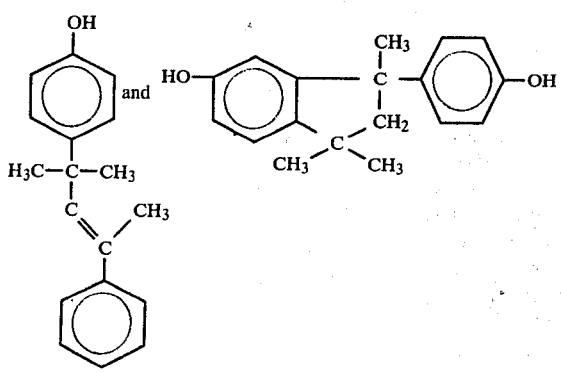

(herein identified as "LD/CD"), and some impurities with unknown structure (herein identified as "color bodies").

Since bisphenol-A is used in making polycarbonate resins by reaction of the latter with either phosgene or diphenyl carbonate, or for making epoxy resins, both resins being used extensively in commercial applications involving molding, casting, and sheet forming purposes, it is highly important that the monomeric bisphenol-A used to make such resins be as pure as possible in order to avoid adverse effects on the properties of the polymers thus obtained.

The preparation of the bisphenol-A by the acid-catalyzed reaction of phenol and acetone is usually carried out in excess phenol (>2 moles per mole acetone). This reaction mixture is subjected to a series of distillation steps to recover crude bisphenol-A which is the starting point for making bisphenol-A of high purity.

The conventional way of recovering a pure bisphenol-A product from crude bisphenol-A involves crystallization in presence of an organic solvent as described in British Pat. Nos. 795,236 and 975,863 and German Pat. No. 1,153,763. According to these patents, crude molten bisphenol-A is first dissolved in a suitable organic solvent. The solution is then cooled to yield pure bisphenol-A crystals, which are recovered by filtration. However, this process suffers in that the crystals produced are fine, powdery and needle-like which are difficult to handle, store and dry. These crystals also permit the organic solvent to occlude during crystallization, which can not be removed readily during the drying step and hence the organic solvent ends up in the downstream polymerization process.

A method which uses water as the crystallization medium for bisphenol-A is described in U.S. Pat. No. 3,326,986. According to this patent, the isolated crude bisphenol-A in molten form is mixed with water and the mixture is cooled to yield large less needle-like crystals of bisphenol-A. Separation of these crystals from the mother liquor followed by an organic solvent wash results in purified bisphenol-A. Although the process described within the above referenced patent avoids occlusion by an organic solvent during the crystal formation step and yields large, less needle-like crystals, the purification is limited, which appears to be due to limited washing of the crystals on the solid/liquid separation equipment after the mother liquor is removed. Theoretically, it should be possible to provide a very effective washing of the crystals obtained from the water crystallization process by repeating the steps of crystal separation, reslurrying the crystals with organic solvent and then crystal separation. However, such a process scheme is not viable since several complex operating steps and high costs are involved.

The present invention demonstrates a simplified method for obtaining high purity bisphenol-A from crude bisphenol-A utilizing an aqueous crystallization process followed by a treatment with an organic washing solvent which is more effective in removing surface impurities than techniques used previously.

DESCRIPTION OF THE INVENTION

The present invention is based on a discovery that bisphenol-A with no detectable impurities may be obtained from crude bisphenol-A by a process comprising the steps of crystallizing crude bisphenol-A in the presence of water, mixing the crystallized bisphenol-A and water slurry with an organic solvent, washing the impurities from the bisphenol-A with an organic solvent by agitating the mixture, settling the mixture so three phases form within the mixture, removing the top phase of the mixture to form a two phase crystal slurry, and separating the crystals from the two-phase crystal slurry; said organic solvent being immiscible with water, lighter than water, and a good solvent medium for the impurities in crude bisphenol-A; and said three phases including a top phase of organic solvent with impurities, a middle phase of aqueous liquid and a bottom phase of BPA crystals in a purified state.

The crude bisphenol-A produced from a BPA synthesis reaction is typically in the form of a liquid residue as, for example, in the case of crude bisphenol-A produced from the acid-catalyzed condensation reaction with phenol and acetone after the excess phenol is removed from the reaction mixture by distillation.

In the typical situation crystallization of crude bisphenol-A can be effected simply by adding water to the molten crude BPA and slowly cooling the mixture to a temperature in the range of 60° C. to 70° C. The quantity of water used is not critical, but preferably equal to one to two times the quantity of crude bisphenol-A to be crystallized on a weight basis. This should produce a sufficiently large buffer zone between the organic solvent and the bisphenol-A crystals. Initially the mixture exists in two phases with the liquid crude bisphenol-A phase resting below the water phase. As the mixture cools crystals form and a slurry of BPA crystals and water, with all the impurities and color bodies adhered to the crystals, is produced.

In the unusual situation, where the crude bisphenol-A produced from a BPA synthesis reaction is in the form of a solid, the crude bisphenol-A must be either remelted and treated as the liquid crude bisphenol-A or remelted in the presence of water and cooled to a temperature in the range of 60° C. to 70° C.

After the crude bisphenol-A is crystallized in the presence of water an organic solvent is added to the water and BPA crystals slurry for the purpose of washing the surface of the crystals of any impurities, including phenol, isomeric diphenols, color bodies, etc., found in crude bisphenol-A. Some of the parameters which define a suitable organic solvent are that the solvent be immiscible in water and lighter than water so that it forms a top surface layer in the presence of water. Another parameter which defines a suitable organic solvent is that the organic solvent must provide a good solvent medium for impurities, such as phenol, isomeric diphenols, color bodies, etc., found in crude bisphenol-A. Some suitable organic solvents are, for example, benzene, butyl acetate, xylene, toluene, etc. Toluene is the preferred solvent for washing the aqueous crystallized bisphenol-A.

Since the organic solvent is separated from the bisphenol-A crystals by the aqueous layer, the mixture of water, crystals and organic solvent must be agitated to bring the crystals into contact with the organic solvent and effectuate washing of the crystals. The mixture is preferably agitated for a period of five to ten minutes to ensure adequate crystal washing. The quantity of organic solvent employed, on a weight basis, is preferably from one to two parts organics solvent per part of crude bisphenol-A.

After agitation the mixture is allowed to settle until three phases form. The top phase being the organic solvent with the impurities and color bodies present within the crude bisphenol-A. The middle phase comprising an aqueous layer which separates the washed crystals from the organic solvent. The bottom phase comprising the bisphenol-A crystals which are now in a purified state, having their impurities washed from their surfaces. These crystals are only water wetted and free of any organic solvent which was used to wash the crystals. The organic solvent is then decanted from the three phase mixture utilizing conventional equipment and a crystal slurry of aqueous liquid and purified bisphenol-A crystals is left remaining. The purified bisphenol-A crystals can be removed from the crystal slurry by employing conventional solid liquid separation equipment such as basket centrifuge.

The process comprising this invention has an advantage in that the entire purification process, including aqueous crystallization, washing with an organic solvent and crystal separation, can take place in one vessel. Also, the quality of the purified bisphenol-A product is enhanced due to more effective contact of the crystals with the organic solvent and the existence of a water buffer phase which separates the bisphenol-A crystals from the impurities in the organic solvent.

The purified bisphenol-A product from this process will also be free of any organic washing solvent and will only be water-wetted. The slightly water wetted crystals need not be dried if used to form polycarbonate since water is utilized in that process.

Although the bisphenol-A crystals obtained as a result of practicing the process described above are usually in a highly purified state, for some crude bisphenol-A samples it is possible there may be impurities that have occluded on to the bisphenol-A crystals during the aqueous crystallization process. In such a situation the process described above can be modified to obtain bisphenol-A crystals with high purity despite the occlusion of impurities.

The process is modified by heating the crystal slurry of bisphenol-A crystals and aqueous liquid that remains after treatment with an organic solvent to a temperature sufficiently high to melt the purified bisphenol-A crystals before they are removed from the crystal slurry. The value of the temperature selected preferably being between 90° C. and 100° C. The heated crystal slurry is then cooled to a temperature sufficiently low to recrystallize the molten bisphenol-A. This temperature is preferably in the range of 60° C. to 70° C. These steps free any of the impurities which have occluded during the aqueous crystallization process upon the bisphenol-A crystals.

The crystallized bisphenol-A is washed with an organic solvent while within the aqueous crystal slurry. This is accomplished by first mixing an organic solvent into the crystal slurry comprising the recrystallized bisphenol-A and water and then agitating the resulting mixture to ensure contact between the organic solvent and the recrystallized bisphenol-A. The quantity of organic solvent employed in this step, on a weight basis, is preferably in the range of one half to one part of organic solvent per part of original crude bisphenol-A started with.

The organic solvent used in this washing step must have properties similar to those of the organic solvent used in the initial washing step. The organic solvent must be immiscible in water, lighter than water, and must be a good solvent medium for the impurities which may have occluded during the aqueous crystallization process. These impurities include phenol, isomeric diphenols, color bodies, etc., which exist within crude bisphenol-A. Suitable organic solvents are, for example, butyl acetate, benzene, xylene, toluene, etc. The preferred organic solvent for this washing step is toluene and the preferred period of agitation to ensure adequate washing of the recrystallized bisphenol-A is between five and ten minutes.

After the recrystallized bisphenol-A crystals are washed the agitated crystal slurry is allowed to settle until three phases form. The top phase being all the organic solvent with the occluded impurities dissolved within it. The middle phase is an aqueous liquid which separates the top phase from the recrystallized bisphenol-A. The recrystallized bisphenol-A forms the lower phase at the bottom of the crystal slurry and is in a highly purified state. The top phase of organic solvent and impurities is removed by decanting the liquid from the three phase crystal slurry of recrystallized bisphenol-A, aqueous liquid and organic solvent. A two phase crystal slurry of aqueous liquid and recrystallized bisphenol-A is left remaining. The highly purified bisphenol-A crystals are removed from the two phase crystal slurry by conventional solid liquid separation equipment, such as a basket centrifuge.

Samples produced from this process approach 100% purity with no impurities being detected by liquid chromotograph analysis, melting point tests, and absorbance values. This invention provides major advantages over the processes described in U.S. Pat. Nos. 354,075, 354,027 and 354,007 since the product of the processes described in these patents is crystallized in the presence of an organic solvent producing small crystals that permit occlusion during crystallization. The product from this invention produces large less needle like crystals and avoids the occlusion of the organic solvent on to the product crystals. The process described in this invention provides more efficient washing of the bisphenol-A crystals than that described in U.S. Pat. No. 3,326,956. Also, this process can be carried out in a simple set up (only one vessel) utilizing simple steps. Finally, this process produces a product which is only water-wetted which need not be completely dried if used to form polycarbonate.

In order that those skilled in the art may better understand the present invention and how it may be practiced, the following examples are given by way of illustration and not by way of limitation.

EXAMPLE I

To a 1,000 mls flask were added 200 gms of water and 200 gms crude BPA of 98% purity with an initial absorbance value of 1.70 and a freezing point of 154.5° C. (Initial absorbance value is the relative color content value which was measured as the absorbance of a 10% solution (5 gms diluted with 50 mls methanol) in a 10 cm cell at 350 nm wave-length.) The flask, being equipped with an agitator, a thermometer, baffles and condensor, was immersed in an oil bath for temperature control. The mixture was heated to around 100° C. to melt all the solids. This was followed by cooling with agitation to effect crystallization of pure BPA. When the crystallization temperature reached 65° C., 300 gms of toluene (at 65° C.) were added to the water/BPA crystals slurry. The mixture was agitated for about 15 minutes and then allowed to settle. Three phases were observed. The top phase was very yellow in color and presumably it was toluene with the impurities and color bodies. The middle phase was a colorless liquid (presumably the water phase) and the bottom phase consisted of white crystalline solids. The top phase was decanted and the BPA product was recovered from the water-BPA crystals slurry with the help of a basket centrifuge. The recovered product had an initial absorbance value of 0.10 and a freezing point of 156.8° C. with no detectable impurities. The quantity of product recovered from this process was 163 gms.

EXAMPLE II

To a 1000 ml flask were added 200 gms of water and 200 gms of crude BPA (% purity: 94, initial absorbance value: 5.68, freezing point: 152° C.). The contents were mixed, heated and cooled to crystallize BPA in a similar manner as in Example I. At 65° C., 700 gms of toluene (at 65° C.) were added to the water BPA crystals slurry. After agitating the mixture for about 15 minutes, the mixture was allowed to settle. The top toluene phase was decanted and 150 gms of BPA product were recovered from the water BPA crystals slurry with the help of a basket centrifuge. The recovered product had an initial absorbance value of 0.15, a freezing point of 156° C. and was over 99% pure.

Repeating the above run with 1200 gms of toluene did not yield better quality BPA product. This indicates that some occlusion of impurities (and color bodies) might have occurred in the crystallization process.

EXAMPLE III

Example II was repeated with 200 gms of crude BPA (% purity: 94, initial absorbance: 5.68, freezing point 152° C.) and 300 gms of toluene. After decanting the top phase, the remaining water BPA crystals slurry was heated again to around 100° C. to melt the crystals. This mixture was then cooled to recrystallize BPA. At 65° C., 200 gms of toluene (at 65° C.) were added. The mixture was agitated and then allowed to settle. The top toluene phase was then decanted and 154 gms of BPA product recovered from the remaining water BPA crystals slurry with the help of a basket centrifuge. The recovered BPA product had an initial absorbance value of 0.10, a freezing point of 157° C. and no detectable impurities.

While the invention has been described in detail and with reference to specific embodiments thereof, it will be apparent to one skilled in the art that various changes and modifications can be made therein without departing from the spirit and scope of the invention.

What we claim as new and desire to secure by Letters Patent of the United States is:

1. A process for recovering bispenol-A in a purified state from water crystallized crude bisphenol-A which comprises the steps of:
    (a) mixing water-crystallized bisphenol-A in the presence of water with an organic solvent, said organic solvent being immiscible in water, lighter than water and a good solvent medium for impurities within crude bisphenol-A,
    (b) agitating the mixture,
    (c) forming three phases in the agitated mixture of step (b),
    (d) removing the top phase of the three phase mixture of step (c), and
    (e) separating purified bisphenol-A crystals from the remaining two phases of step (d).

2. A process in accordance with claim 1 wherein said organic solvent is toluene.

3. A process in accordance with claim 1 wherein said organic solvent mixed into said water crystallized bisphenol-A in the presence of water is in an amount within the range of 1 to 2 parts thereof per part of bisphenol-A on a weight basis.

4. A process for recovering bisphenol-A in a highly purified state from water crystallized crude bisphenol-A which comprises the steps of:

(a) mixing water-crystallized bisphenol-A in the presence of water with an organic solvent, said organic solvent being immiscible in water, lighter than water and a good solvent medium for impurities within crude bisphenol-A, (b) agitating the mixture, (c) forming three phases in the agitated mixture of step (b), (d) removing the top phase of the three phase mixture of step (c), (e) heating the remaining two phase crystal slurry of step (d) to a temperature sufficiently high to melt the bisphenol-A crystals within, (f) cooling the heated two phase crystal slurry of step (e) to a temperature sufficiently low to crystallize the molten bisphenol-A, (g) mixing a fresh organic solvent into the cooled two phase crystal slurry of step (f) said fresh organic solvent being immiscible with water, lighter than water and a good solvent medium for impurities within the bisphenol-A crystals, (h) agitating the mixture of step (g), (i) forming three phases in the agitated mixture of step (h), (j) removing the top phase of the three phase mixture of step (i), and (k) separating highly purified bisphenol-A crystals from the remaining two phases of step (j).

5. A process in accordance with claim 4 wherein said fresh organic solvent is toluene.

6. A process in accordance with claim 4 wherein the temperature selected to melt the said purified bisphenol-A crystals is within the range of 90° C. to 100° C.

* * * * *